United States Patent [19]

Kadokura

[11] Patent Number: 6,002,036
[45] Date of Patent: Dec. 14, 1999

[54] PROCESS FOR PRODUCING BIS(ALKYL-CYCLOPENTADIENYL)RUTHENIUM COMPLEXES AND PROCESS FOR PRODUCING RUTHENIUM-CONTAINING FILMS BY USING THE SAME

[75] Inventor: Hidekimi Kadokura, Tokyo, Japan

[73] Assignee: Kabushikikaisha Kojundokagaku Kenkyusho, Saitama, Japan

[21] Appl. No.: 09/264,557

[22] Filed: Mar. 8, 1999

Related U.S. Application Data

[62] Division of application No. 09/097,407, Jun. 15, 1998.

[30] Foreign Application Priority Data

Jul. 17, 1997 [JP] Japan ..................... 9-225493

[51] Int. Cl.$^6$ .............. C07F 15/00; C07F 17/00
[52] U.S. Cl. ....................... 556/136; 427/248.1
[58] Field of Search ................ 556/136; 427/248.1

[56] References Cited

U.S. PATENT DOCUMENTS 2,912,449  11/1959  Sweeney ................ 260/439
3,306,917  2/1967   Shapiro et al. ............ 260/429
4,992,305  2/1991   Erbil ........................ 427/252

*Primary Examiner*—Porfirio Nazario-Gonzalez
*Attorney, Agent, or Firm*—Fattibene & Fattibene; Paul A. Fattibene; Arthur T. Fattibene

[57] ABSTRACT

To provide Ru compounds which are in the form of a liquid at room temperature to be used in forming Ru and $RuO_2$ films for electrodes in semiconductor devices by the CVD method and a process for producing these compounds.

Because of being a liquid at room temperature and having a sufficient vapor ressure at about 100° C., bis(ethylcyclopentadienyl)ruthenium or bis(isopropylcyclopentadienyl)ruthenium can be quantitatively supplied via gas bubbling or with the use of a liquid mass flow controller as a feedstock in the CVD method and thermally decomposed on a substrate at 600° C. in a hydrogen atmosphere to give pure Ru films. These compounds can be obtained at a high yield by reacting respectively ruthenium trichloride hydrate and ethylcyclopentadiene or isopropylcyclopentadiene with a zinc powder in an alcohol solvent at −30 to 0° C.

4 Claims, No Drawings

PROCESS FOR PRODUCING BIS(ALKYL-CYCLOPENTADIENYL)RUTHENIUM COMPLEXES AND PROCESS FOR PRODUCING RUTHENIUM-CONTAINING FILMS BY USING THE SAME

This application is a divisional of application Ser. No. 09/097,407 filed Jun. 15, 1998.

FIELD OF THE INVENTION

This invention relates to a process for producing a bis (ethylcyclopentadienyl)ruthenium complex and a bis (isopropylcyclopentadienyl)ruthenium complex and a process for producing ruthenium-containing films by the chemical vapor deposition method (hereinafter referred to simply as "the CVD method") by using the same.

BACKGROUND OF THE INVENTION

With the recent tendency toward ultra-large-scale integrated circuits (ULSI), studies are under way to develop (Ba, Sr)$TiO_3$ films having high dielectric constants as capacitors and Ru and/or $RuO_2$ films are frequently employed as electrodes thereof. It has been a practice to produce these Ru films by the Ru metal sputtering method, while the $RuO_2$ films are produced by the reactive sputtering method of Ru metal in many cases. In further microscaled cases, however, it is expected that the desired step coverage or mass-productivity can be achieved by the CVD method. As the volatile ruthenium compounds to be used in the CVD method, investigations are in progress on tris (dipivaloylmethanato)ruthenium $Ru(dpm)_3$ and bis (cyclopentadienyl)ruthenium $Ru(C_5H_5)_2$. Nakabayashi et al. reported that an Ru film was formed on an Si substrate at 600° C. by using $Ru(dpm)_3$ by the CVD method and then oxygen was introduced thereinto to give an $RuO_2$ film on the Ru (Proceedings of the 55th Symposium of Applied Physics in Autumn of 1994, p. 347, 19p-M-9 (1994)). However, $Ru(dpm)_3$ has a melting point of 168° C. and thus occurs as solid crystals at room temperature. Because of having a vapor pressure of 0.1 Torr at about 136° C., it is supplied via sublimation.

D. E. Trent, B. Paris and H. H. Krause reported that a ruthenium metallic specular film with a purity of 99.99% was formed on a vycor glass substrate at 595° C. by the CVD method by supplying the sublimated vapor from $Ru(C_5H_5)_2$ maintained at 94° C. together with hydrogen gas (Inorg. Chem., 3, 1057 (1964)).

W. -C. Shin and S. -G. Yoon reported that $Ru(C_5H_5)_2$ was subjected to CVD at about 350° C. in an oxygen gas to thereby form an $RuO_2$ film of 200 nm on an $SiO_2$/Si, MgO substrate (9th International Symposium on Integrated Ferroelectrics (Santa Fe, N.M.. March, 1997), p. 104).

U.S. Pat. No. 5,130,172 has disclosed a process for coating a substrate with a metal comprising: maintaining the substrate at a temperature up to 190° C.; exposing this substrate to a vaporized organometallic compound represented by the formula $L_nMR_m$ obtained by heating to a temperature up to 100° C.; then exposing the substrate to a hydrogen gas at a temperature up to 100° C.; and reacting the organometallic compound with hydrogen to thereby form a metal film. In the above formula $L_nMR_m$, L is hydrogen, ethylene, allyl, methylallyl, butadienyl, pentadienyl, cyclopentadienyl, methylcyclopentadienyl, cyclohexadienyl, hexadienyl, cycloheptatrienyl or a derivative of these compounds having at least one alkyl side chain having less than five carbon atoms; M is a metal that can readily cycle between two oxidation states and can catalyze hydrogenation of hydrocarbon ligands; R is methyl, ethyl, propyl or butyl; n is an integer from 0 to the valence of the metal; m is an integer from 0 to the valence of the metal; and m plus n must equal the valence of the metal. The cyclopentadienylruthenium compounds given in the claims specifying the same are cyclopentadienyl (methylcyclopentadienyl)ruthenium $(C_2H_5)Ru(C_5H_4CH_3)$, ruthenocenylacetylene $(C_5H_5)Ru(C_5H_4CCH)$, ethenylruthenocene $(C_2H_5)Ru(C_5H_4CHCH_2)$, bis (methylcyclopentadienyl)ruthenium $Ru(C_5H_4CH_3)_2$ and ethylruthenocene $(C_5H_5)Ru(C_5H_4CH_2CH_3)$.

Table 1 shows the melting point of each of the compounds cited above shown in Dictionary of Organometallic Compounds, vol. 3 (2nd Ed., 1966, Chapman & Hall). Namely, all of these compounds except ethylruthenocene are solids at room temperature of 25° C.

TABLE 1

| | M.p. (° C.) |
|---|---|
| bis(cyclopentadienyl)ruthenium $Ru(C_5H_5)_2$ | 199–200 |
| bis(methylcyclopentadienyl)ruthenium $Ru(C_5H_4CH_3)_2$ | 61–63 |
| cyclopentadienyl(methylcyclopentadienyl)-ruthenium $(C_5H_5)Ru(C_5H_4CH_3)$ | 41–42 |
| ethenocenylacetylene $(C_5H_5)Ru(C_5H_4CCH)$ | 73–74 |
| ethenylruthenocene $(C_5H_5)Ru(C_5H_4CHCH_2)$ | 53.5–54.5 |
| ethylruthenocene $(C_5H_5)Ru(C_5H_4CH_2CH_3)$ | 12–12.5 |

The supply of the starting compound via sublimation in the CVD method is inferior in quantitative supply, controllability and mass-productivity to the liquid supply system or evaporation supply system with the use of a carrier gas bubbling into the liquid. Accordingly, it is required to employ a starting compound which is a liquid at the step of supply at room temperature and has a sufficient vapor pressure. Moreover, it is necessary that the starting compound can be easily produced on a mass scale. Among the known cyclopentadienylruthenium compounds capable of forming an Ru film by the CVD method, none but ethylruthenocene is a liquid at room temperature of 55° C. and has a vapor pressure.

However, ethylruthenocene is poor in mass-productiveness. According to V. Mark and M. D. Raush, ethylruthenocene is synthesized by reducing cyclopentadienyl(acetylcyclopentadienyl)ruthenium $Ru(C_5H_5)(C_5H_4COCH_3)$ with $LiAlH_4+AlCl_3$ in diethyl ether [Inorg. Chem., vol. 3, 1067 (1964)]. Namely, it is necessary to use a specific cyclopentadienylruthenium compound as an intermediate, which brings about problems in mass-productiveness and production cost. That is to say, there has been known so far no cyclopentadienylruthenium compound which can be easily produced on a mass scale, is a liquid at room temperature and has a sufficient vapor pressure.

An object of the present invention is to specify cyclopentadienylruthenium compounds which are liquids at room temperature of 25° C., have sufficient vapor pressures, can be easily produced on a mass scale and are usable in forming Ru and $RuO_2$ films by the CVD method and provide a process for forming Ru and $RuO_2$ films by the CVD method with the use of these compounds. Another object of the present invention is to provide a process for producing these specific compounds being excellent in mass-productivity.

SUMMARY OF THE INVENTION

The present inventor has been studying the synthesis of organometallic compounds and CVD with the use of the same for a long time. To solve the above problems, the inventor synthesized and purified bis(ethylcyclopentadienyl)ruthenium Ru(C$_2$H$_5$C$_5$H$_4$)$_2$, which is a publicly known compound with an undetermined melting point, and bis(isopropylcyclopentadienyl) ruthenium Ru(iC$_3$H$_7$C$_5$H$_4$)$_2$, which is an unknown compound, and measured the melting points and vapor pressures thereof. As a result, they revealed that these compounds have favorable physical properties. Then they formed Ru and RuO$_2$ films by the CVD method with the use of these compounds and thus found out that stable and good films could be obtained thereby, thus completing the present invention. Accordingly, the present invention has been established based on the finding that bis(ethylcyclopentadienyl)ruthenium Ru(C$_2$H$_5$C$_5$H$_4$)$_2$ and bis(isopropylcyclopentadienyl) ruthenium Ru(iC$_3$H$_7$C$_5$H$_4$)$_2$ are usable as the material which is a liquid at room temperature of 25° C. to be used in forming Ru and RuO$_2$ films by the CVD method.

Although bis(ethylcyclopentadienyl)ruthenium is a known compound processes for the synthesis of which are disclosed in two reports, its melting point has never been reported so far. One of the processes for synthesizing this compound comprises reducing bis(acetylcyclopentadienyl) ruthenium Ru(C$_5$H$_4$COCH$_3$)$_2$ with NaBH$_4$—H$_2$SO$_4$ (G. B. Shul'pin, Zh. Obsch. Khim., 51, 2152 (1981)).

In another process, this compound is synthesized by a ligand displacement reaction between RuCl3 and bis(ethylcyclopentadienyl)iron Fe(C$_2$H$_5$C$_5$H$_4$)$_2$ (G. J. Ganthier, Chem. Commun. 690 (1969)).

The bis(acetylcyclopentadienyl)ruthenium Ru(C$_5$H$_4$COCH$_3$)$_2$ and bis(ethylcyclopentadienyl)iron Fe(C$_2$H$_5$C$_5$H$_4$)$_2$ employed as the intermediates in these syntheses are both poor in mass-productivity. Moreover, use of an iron compound brings about another problem that the thus obtained product would be contaminated with other iron compounds which have similar properties and thus can be hardly eliminated. In such a case, therefore, a ruthenium compound with a high purity can be hardly obtained.

Bis(isopropylcyclopentadienyl)ruthenium Ru(iC$_3$H$_7$C$_5$H$_4$)$_2$ is a publicly unknown compound and neither any method for synthesizing the same nor its melting point has been reported so far.

DETAILED DESCRIPTION OF THE INVENTION

The compounds to be used in the present invention for producing ruthenium-containing films are bis(ethylcyclopentadienyl)ruthenium Ru(C$_2$H$_5$C$_5$H$_4$)$_2$ and bis(isopropylcyclopentadienyl)ruthenium Ru(iC$_3$H$_7$C$_5$H$_4$)$_2$.

The present invention further provides a process for producing bis(ethylcyclopentadienyl)ruthenium Ru(C$_2$H$_5$C$_5$H$_4$)$_2$ and bis(isopropylcyclopentadienyl) ruthenium Ru(iC$_3$H$_7$C$_5$H$_4$)$_2$ with high mass-productivity. This process of the present invention originates in a method for synthesizing bis(cyclopentadienyl)ruthenium Ru(C$_5$H$_5$)$_2$ reported by P. Pertici, G. Vitulli and L. Porri (J. C. S. Chem. Comm., 846 (1975)). That is to say, Pertici et al. disclosed that bis(cyclopentadienyl)ruthenium Ru(C$_5$H$_5$)$_2$ was obtained at a yield of 75%, based on ruthenium trichloride, by reacting ruthenium trichloride trihydrate with cyclopentadiene in ethanol in the presence of a zinc powder for 0.5 hour under stirring at 20° C.

The present inventor performed the reaction of Pertici et al. but employing ethylcyclopentadiene or isopropylcyclopentadiene as a substitute for the cyclopentadiene. Then a rapid exothermic reaction occurred and a solid polymer-like product was formed in each case. Namely, the desired bis(ethylcyclopentadienyl)ruthenium Ru(C$_2$H$_5$C$_5$H$_4$)$_2$ or bis(isopropylcyclopentadienyl)ruthenium Ru(iC$_3$H$_7$C$_5$H$_4$)$_2$ could not be obtained thereby.

Thus, the present inventor examined various factors affecting the reaction yield and consequently found out that the reaction temperature and the reduction speed by the zinc powder were highly important. By regulating these factors, the desired products were obtained at high yields of 70% or above.

It is estimated that the reaction proceeds in an alcohol solvent in accordance with the following formula.

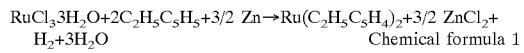

$$RuCl_3 3H_2O+2C_2H_5C_5H_5+3/2\ Zn \rightarrow Ru(C_2H_5C_5H_4)_2+3/2\ ZnCl_2+H_2+3H_2O$$

Chemical formula 1

The reaction temperature preferably ranges from −30 to 0° C. It is not desirable to effect the reaction at 0° C. or above, since side reactions would gain predominance in such a case. On the other hand, a reaction temperature not higher than −30° C. is not desirable, since the reaction proceeds slowly at such a temperature and thus becomes unsuitable for mass production. The zinc powder is added not at once at the initiation of the reaction but in portions. It is not preferable to add the zinc powder at once, since the reaction rate and temperature cannot be controlled in such a case. It is needed that the zinc powder is added at such intervals that the reaction temperature is maintained within the range as specified above. The reaction is carried out for about 30 minutes to 2 hours. Finally, the reaction system is maintained at around 10° C. for 10 to 30 minutes for aging to thereby complete the reaction.

The starting ruthenium chloride hydrate may be an arbitrary one so long as it is soluble in alcohols. Namely, use may be made of not only ruthenium chloride trihydrate but also mixtures of mono- to trihydrates which can be easily produced and obtained industrially. Since the reaction is effected in a system containing a little moisture, cyclopentadienyl compounds of zinc and a number of transition metals potentially formed as the by-products are decomposed thereby, which brings about a benefit that the obtained ruthenium compound has a high purity.

Ethylcyclopentadiene and isopropylcyclopentadiene can be synthesized by publicly known methods. To obtain the target product at a high yield, it is preferable to feed ethylcyclopentadiene or isopropylcyclopentadiene in an amount at least twice as much as the stoichiometric amount.

As the alcohol employed as the solvent, use may be made of methanol, ethanol, isopropanol, etc. It is preferable to use the alcohol in such an amount that the starting ruthenium chloride hydrate can be sufficiently dissolved therein and the zinc chloride thus formed can be also sufficiently dissolved therein. When measured by the present inventors, 28 g of ruthenium chloride hydrate was soluble in 100 ml of ethanol at 23° C. According to Kagaku Daijiten (Encyclopedic Dictionary of Chemistry; Kyoritsu Shuppan, 1971), 80 g of zinc chloride is soluble in 100 ml of ethanol at 12.5° C. An increase in the amount of the alcohol solvent brings about an advantage that an increase in the liquid temperature due to the heat of reaction can be reduced. In this case, however, the reaction volume efficiency is lowered.

Thus, the adequate amount of the alcohol employed is to be determined by taking these factors into consideration.

The zinc powder may be an arbitrary one, so long as it has a particle size ensuring uniform suspension and smooth progress of the reaction. Use may be made therefor of those being 100-mesh under (i.e., passing through a sieve with an opening size of 147 μm) or 200-mesh under (i.e., passing through a sieve with an opening size of 74 μm). It is preferable to use a zinc powder with a high purity, since the purity of the ruthenium compound thus obtained is affected thereby. A 5-nine zinc powder product of 200-mesh under is industrially available.

The reaction product is in the form of a liquid at room temperature. Thus, the trace amount of the unreacted zinc powder is eliminated therefrom by decantation. Subsequently, the alcohol is distilled off under reduced pressure and hexane is added to the residue to thereby dissolve the target product. Next, a heavy and viscous slurry mainly consisting of zinc chloride particles is decanted and the supernatant is distilled off under reduced pressure followed by distillation in vacuo.

The desired bis(ethylcyclopentadienyl)ruthenium $Ru(C_2H_5C_5H_4)_2$ and bis(isopropylcyclopentadienyl) ruthenium $Ru(iC_3H_7C_5H_4)_2$ are each in the form of a pale yellow liquid having a viscosity of about 100 cP at room temperature (25° C.). These compounds are relatively stable and would not react with water in the atmosphere. They remain stable when heated to 200° C. or above.

Table 2 shows the physical data of these compounds relating particularly to CVD.

TABLE 2

| | M.p. (° C.) | Vapor pressure (Torr/° C.) |
|---|---|---|
| $Ru(C_2H_5C_5H_4)_2$ | 6 | 0.3/100 |
| $Ru(iC_3H_7C_5H_4)_2$ | 21 | 0.2/100 |

The present invention further provides a process for synthesizing highly pure bis(ethylcyclopentadienyl) ruthenium $Ru(C_2H_5C_5H_4)_2$ or bis (isopropylcyclopentadienyl)ruthenium $Ru(iC_3H_7C_5H_4)_2$ usable in electronic devices.

Although a zinc powder is employed as one of the reactants in this process, the zinc content in the desired compound can be regulated to 1 ppm or below after purifying by distillation. Also, a number of transition metals other than iron can be decomposed by water, which makes it possible to regulate the content thereof to 1 ppm or below. Because of being similar in reactivity and vapor pressure of bis(alkylcyclopentadienyl)iron to ruthenium compounds, iron can be hardly eliminated therefrom. It is therefore preferable to use materials contaminated with little iron.

The present invention also provides a process for producing ruthenium-containing films by the CVD method with the use of bis(ethylcyclopentadienyl)ruthenium $Ru(C_2H_5C_5H_4)_2$ or bis(isopropylcyclopentadienyl) ruthenium $Ru(iC_3H_7C_5H_4)_2$. This process comprises bubbling a carrier gas under reduced pressure into either compound maintained at 80 to 150° C., thus evaporating the compound together with the carrier gas, feeding the mixture into a pyrolytic reactor and effecting pyrolysis on a substrate at 500 to 600° C. to thereby form an Ru-containing film. Instead of the evaporation feeding by bubbling, the compound may be fed and evaporated by using a liquid mass flow controller.

To form an Ru film in the present invention, the pyrolysis on the substrate is carried out in a hydrogen-containing atmosphere. It is also possible to use hydrogen as the carrier gas. A metallic Ru film obtained in the hydrogen atmosphere is a highly pure metallic film having a fair specular surface and little contaminated with metallic impurities. An $RuO_2$ film can be obtained by effecting pyrolysis in the coexistence of an oxygen gas or once forming an Ru film followed by thermally treating it in an oxygen-containing atmosphere.

EXAMPLE 1

Production of bis(ethylcyclopentadienyl)ruthenium $Ru(C_2H_5C_5H_4)_2$:

A three-necked flask (500 ml) provided with a reflux condenser, a thermometer, a solid powder inlet and stirring blades was purged with argon in vacuo and then 200 ml of ethanol was fed thereinto. Next, 25.0 g (95.6 mmol) of ruthenium chloride trihydrate was added thereto and dissolved therein. After cooling this reaction flask to -30° C., 40 g (425 mmol) of ethylcyclopentadiene was introduced thereinto. Subsequently, 9.55 g (146 mmol) of a zinc powder (200-mesh under, 5-nine in purity) was divided into seven portions and one portion thereof was added from the inlet while stirring the contents of the flask and maintaining the liquid temperature to -25 to -10° C. The residual portions of the zinc powder were added at intervals of about 5 to 10 minutes. Thus, the addition of the zinc powder was completed within 1 hour. During this period, the liquid temperature was maintained at -25 to -10° C. After maintaining the liquid reaction mixture at 10° C. for 20 minutes, it was allowed to stand followed by the recovery of the liquid layer by decantation. Thus, nothing but about 0.1 g of the unreacted zinc powder remained in the reaction flask. Then most of the ethanol and the unreacted ethylcyclopentadiene were distilled off under reduced pressure from the liquid thus taken up. To the residual viscous slurry was added 500 ml of hexane followed by dissolution by stirring. After allowing the mixture to stand, the supernatant was recovered by decantation to give a black and viscous slurry (fine particles of zinc chloride) as the residue. From the supernatant were distilled off hexane, etc. under reduced pressure and a fraction at around 100° C. was obtained by vacuum distillation at about 0.1 Torr.

This fraction was a pale yellow liquid (19.7 g) showing an Ru content of 34.1% by weight (theoretical value: 35.2% by weight). It was bis(ethylcyclopentadienyl)ruthenium $Ru(C_2H_5C_5H_4)_2$ and the amount thereof (68 mmol) corresponded to a yield of 71%. This product had a density of 1.4 g/cm$^3$ and a melting point of 6° C. It was liable to become a supercooled liquid.

When measured with an isoteniscope, it showed a vapor pressure of 0.3 Torr/100° C.

This liquid had a high purity with the following contaminants (expressed in ppm):

Fe<1, Zn<1, Al<1, Na<1, Ca 1, Mo<3, Pd<3.

EXAMPLE 2

Production of bis(isopropylcyclopentadienyl)ruthenium $Ru(iC_3H_7C_5H_4)_2$:

The reaction and recovery procedures of Example 1 were repeated but using 45 g (416 mmol) of isopropylcyclopentadiene as a substitute for the ethylcyclopentadiene. A fraction at around 110° C. was obtained by vacuum distillation at about 0.1 Torr.

This fraction was a pale yellow liquid (22.5 g) showing an Ru content of 31.0% by weight (theoretical value: 32.0% by weight). It was bis(isopropylcyclopentadienyl)ruthenium $Ru(iC_3H_7C_5H_4)_2$ and the amount thereof (71 mmol) corresponded to a yield of 74%. This product had a density of 1.26 g/cm$^3$ and a melting point of 21° C. It was liable to become a supercooled liquid. When measured with an isoteniscope, it showed a vapor pressure of 0.2 Torr/100° C.

COMPARATIVE EXAMPLE

Production of bis(ethylcyclopentadienyl)ruthenium:

The reaction and recovery procedures of Example 1 were repeated but feeding the ethylcyclopentadiene at 20 to 30° C.

and effecting the reaction at 20 to 30° C. After distilling off the recovered hexane, vacuum distillation was carried out. However, only 0.2 g of a pale yellow liquid was obtained thereby. Thus, it was considered that no desired bis(ethylcyclopentadienyl)ruthenium $Ru(C_2H_5C_5H_4)_2$ but polymers insoluble in hexane were formed as the by-products.

EXAMPLE 3
Production of pure Ru film by the CVD method with the use of bis(ethylcyclopentadienyl)ruthenium $Ru(C_2H_5C_5H_4)_2$:

The whole reaction system involving a feedstock container and a pyrolytic reactor was maintained under reduced pressure (10 Torr) by using a rotary vacuum pump and pressure-control valves. The feedstock container packed with 15 g of bis(ethylcyclopentadienyl) ruthenium $Ru(C_2H_5C_5H_4)_2$ was introduced into a thermostat at 100° C. and a carrier hydrogen gas was bubbled thereinto at 10 sccm. The bis(ethylcyclopentadienyl)ruthenium $Ru(C_2H_5C_5H_4)_2$ was evaporated together with this gas and introduced into the pyrolytic reactor in which the bis(ethylcyclopentadienyl) ruthenium was decomposed on a quartz substrate heated to 600° C. Thus a pure Ru film of 50 nm in thickness was formed within 20 minutes. It was identified as metallic Ru by XRD. When the film was dissolved and metallic impurities were analyzed at an order of ppm, no metallic impurities other than Ru was detected therefrom. This film had a glossy metallic color and an even and smooth surface was obtained at a high reproducibility, which proved that the liquid material was fed via bubbling in a well-controlled state.

EXAMPLE 4
Production of $RuO_2$ film by the CVD method with the use of bis(isopropylcyclopentadienyl)ruthenium $Ru(iC_3H_7C_5H_4)_2$:

Bis(isopropylcyclopentadienyl)ruthenium $Ru(iC_3H_7C_5H_4)_2$, which was used as a substitute for the bis(ethylcyclopentadienyl)ruthenium $Ru(C_2H_5C_5H_4)_2$ employed in Example 3, was quantitatively fed with a liquid mass flow controller. Then it was evaporated in an evaporator at 180° C. and fed onto the heated substrate (380° C.) in the pyrolytic reactor of Example 3. Oxygen gas was simultaneously fed thereinto and thus CVD was effected in an oxygen-containing atmosphere. Thus a $RuO_2$ film of 70 nm in thickness was formed within 20 minutes. It was identified by XRD. When the impurities in the film were analyzed, it was proved as an oxide film having a high purity of 5-nine or above.

The bis(ethylcyclopentadienyl)ruthenium $Ru(C_2H_5C_5H_4)_2$ and bis(isopropylcyclopentadienyl) ruthenium $Ru(iC_3H_7C_5H_4)_2$ synthesized in the present invention are each a liquid at room temperature and has a sufficient vapor pressure at about 100° C. Thus, these compounds can be quantitatively supplied as a CVD material by gas bubbling or with the use of a liquid mass flow controller to give ruthenium-containing films on a substrate by pyrolysis. Namely, the present invention makes it possible to form pure Ru films by the CVD method excellent in mass-productivity.

The invention claimed is:

1. A process for producing bis(alkylcyclopentadienyl) ruthenium complexes which comprises reacting ruthenium trichloride hydrate and ethylcyclopentadiene or isopropylcyclopentadiene with a zinc powder in an alcohol solvent.

2. The process for producing bis(alkylcyclopentadienyl) ruthenium complexes as set forth in claim 1 wherein said a bis(alkylcyclopentadienyl) ruthenium complexes are a bis(ethylcyclopentadienyl) ruthenium complex and a bis(isopropylcyclopentadienyl) ruthenium complex.

3. The process for producing bis(alkylcyclopentadienyl) ruthenium complexes as set forth in claim 1 wherein said zinc powder is added in portions and the reaction is effected at a temperature of from −30 to 0° C.

4. The process for producing bis(alkylcyclopentadienyl) ruthenium complexes as set forth in claim 1 wherein said bis(alkylcyclopentadienyl) ruthenium complexes are highly pure ones containing not more than 10 ppm of metallic impurities in total.

* * * * *